United States Patent [19]

Marsoner

[11] Patent Number: 4,632,807
[45] Date of Patent: Dec. 30, 1986

[54] OPTICAL SENSOR FOR FLUORESCENCE MEASUREMENTS

[75] Inventor: Hermann Marsoner, Steinberg, Austria

[73] Assignee: AVL AG, Schaffhausen, Switzerland

[21] Appl. No.: 563,931

[22] Filed: Dec. 21, 1983

[30] Foreign Application Priority Data

Dec. 28, 1982 [AT] Austria .................................. 4712/82

[51] Int. Cl.$^4$ ............................................. G01N 21/62
[52] U.S. Cl. ......................................... 422/68; 422/83;
422/91; 436/172; 250/458.1
[58] Field of Search .................... 250/373, 461.1, 458.1;
356/306, 317, 318, 417; 422/83, 86, 87, 91, 68;
436/172

[56] References Cited

U.S. PATENT DOCUMENTS

| | | | |
|---|---|---|---|
| 3,725,658 | 4/1973 | Stanley et al. | 422/83 |
| 3,854,050 | 12/1974 | Peterson et al. | 250/461.2 |
| 4,003,707 | 1/1977 | Lubbers et al. | 356/318 |
| 4,255,053 | 3/1981 | Lubbers et al. | 356/318 |
| 4,269,516 | 5/1981 | Lubbers et al. | 356/39 |
| 4,306,877 | 12/1981 | Lubbers | 422/91 |

FOREIGN PATENT DOCUMENTS 106086 5/1974 Fed. Rep. of Germany .
2508637 11/1979 Fed. Rep. of Germany .

Primary Examiner—F. L. Evans
Assistant Examiner—Joel L. Harringa
Attorney, Agent, or Firm—Watson, Cole, Grindle & Watson

[57] ABSTRACT

In an optical sensor used mainly for determining the partial pressure of $O_2$ or $CO_2$ in respiratory gas includes a sample measuring chamber through which sample medium to be analyzed flows or into which it is fed, a reference measuring chamber containing a reference gas or a reference liquid of constant composition, a light source, a unitary excitation filter positioned between the light source and first sides of both the sample measuring chamber and the reference measuring chamber, a single fluorescent sensor element on the second sides of both the sample measuring chamber and the reference measuring chamber, and first and second detectors for detecting the fluorescence radiation from the fluorescent sensor element respectively based on the light passing thereto from the sample measuring chamber and the reference measuring chamber.

7 Claims, 3 Drawing Figures

OPTICAL SENSOR FOR FLUORESCENCE MEASUREMENTS

BACKGROUND OF THE INVENTION

This invention relates to an optical sensor, used mainly for determining the partial pressure of $O_2$ or $CO_2$ in respiratory gas and wherein a light source is used for radiating excitation light via at least one excitation filter into a measuring chamber containing the sample medium to be analyzed, i.e., a gas or liquid. The flourescence radiation excited in a fluorescence indicator and extinguished or reduced by the medium to be analyzed is transmitted to a photodetector via at least one emission filter. A reference measuring chamber is provided in addition to the measuring chamber, which is also exposed to excitation light from the same light source and is also provided with a fluorescence indicator whose fluorescence radiation is transmitted to a reference photodetector via at least one reference emission filter. The signals of the photodetector and the reference signals of the reference photodetector are fed into an evaluation unit for evaluation relative to each other.

DESCRIPTION OF THE PRIOR ART

Optical sensors for measuring gas partial pressures in liquids or gases are known; above all, they are used for determination of the oxygen partial pressure in liquids and gases by optical means based on the principle of fluorescence extinction by molecular oxygen. Suitable measuring devices are described, e.g., in German laid-open print No. 2 508 637. Furthermore, German Patent Specification No. 106.086 describes a probe of the above type in which a fluorescence indicator is contained in a measuring and in a reference chamber, the measuring chamber being connected to the sample medium via a membrane. The reference measuring chamber is completely sealed. In another variant of this patent specification both chambers may be closed by a plate carrying the fluorescence indicator which is sealed against the sample medium, however, in the area of the reference chamber. In this case there is no difference between the two chambers, since the sample medium cannot enter the chambers.

The arrangements of the known type are characterized by certain disadvantages, however, as fluctuations in the intensity of the light source, changes in the sensor elements over time which are independent of the sample medium and, above all, temperature fluctuations in the sensor elements, will influence the result of the measurement. Besides, the geometry of the path of excitation and fluorescence light is unfavorable.

A method of compensating intensity fluctuations of a light source during fluorescence measurement may consist of detecting the intensity of the light emitted by the light source by means of another light-measuring device and by comparing the measured signal with the signal of this reference measuring cell. It is possible, for example, to divide the fluorescence signal by the reference signal (analog method) which will result in a fluorescence signal standardized to the intensity of the excitation light.

With this kind of synchronous measurement of excitation and fluorescence light changes over time in the intensity of the excitation light may be compensated; this does not apply, however, to changes over time in the sensor element proper, e.g., $pO_2$-independent changes, which may occur as a consequence of photomechanical fading or temperature fluctuations.

SUMMARY OF THE INVENTION

It is an object of the present invention to produce an optical sensor taking into account both changes over time in the intensity of the excitation light and changes in the fluorescence intensity of the sensor element which are independent of the medium to be analyzed, e.g., oxygen-containing respiratory gas, and may be caused by temperature fluctuations, for example, and further to simplify the design in order to improve operation and geometry of the sensor.

In an optical sensor of the aforementioned type this is achieved under the present invention mainly by providing that both the measuring chamber through which the sample medium is passed, or rather into which it is fed, and the reference measuring chamber containing a reference gas or a reference liquid of constant composition, are closed either by two identical sensor elements containing a fluorescence indicator—one sensor element for each chamber—or by a discrete area each of one single measuring element containing a fluorescence indicator, the two areas being separated from each other, and by further providing that the fluorescence radiation is transmitted to the photodetectors from that side of the sensor elements facing away from the measuring or reference measuring chamber.

This will ensure great simplicity of design of the sensor proposed by this invention whose measuring and reference measuring chambers are closed by one common or two identical sensor elements containing a fluorescence indicator, the sample medium being fed into the measuring chamber and the fluorescence radiation being detected on that side of the sensor element facing away from the measuring and reference chambers, thereby achieving a simple configuration with a clear and functionally adequate arrangement of the sensor components. Due to the particular arrangement of the sensor elements the sensor described by the present invention will yield measurement values which are independent of differences in the design or operational state of two sensor elements that are operated separately and are not matched to each other. The sensor design is simplified by detecting the fluorescence radiation on the side of the sensor elements facing away from the measuring chamber or reference measuring chamber, which will also enable the sample medium to be measured in a simple manner while flowing through the measuring chamber.

In a preferred embodiment of the invention the light source is positioned symmetrically to the measuring chamber and the reference measuring chamber. The excitation filters for the measuring and reference chambers are preferably combined into filters for common use by both chambers. This will ensure that errors of measurement resulting from the configuration of the optical sensor may be largely eliminated.

A further embodiment of the invention provides for thermostatic control of the temperature of the sensor elements, whereby measurement errors due to temperature changes will also be eliminated. In another preferred embodiment the sensor elements are (or the single measuring element is, respectively) mounted in a sensor housing whose temperature is maintained constant by means of a thermostat. Temperature effects may be further eliminated by maintaining the measuring and reference chambers at the same, preferably constant, temperature by means of a thermostat, preferably in a thermostat-controlled sensor housing. Measuring accuracy may be increased by the use of identical components for the emission filters and photodetectors, or reference emission filters and reference photodetectors, for both measuring and reference chambers, as is proposed by the present invention.

According to a further embodiment of the invention a simple design of the optical sensor is achieved by placing the sensor element, the emission filters, the reference emission filters, the photodetector and the reference photodetector in a common sensor housing which is attached to a light housing containing the light source, the excitation filters, the measuring chamber and the reference measuring chamber such that the sensor housing may be tilted and arrested in its operating position. Operation is made easier if, in the arrested position of the tiltable sensor housing, the sensor element acts as a cover of the rear end of the measuring chamber and the reference chamber, as seen in the direction of radiation from the light source.

Measurement accuracy may be improved if the sensor element comprises a thin coat of a polymer material containing an oxygen indicator, which has been applied to a transparent rigid carrier. Errors may also be prevented by closing the front openings of the measuring chamber and the reference measuring chamber—as seen in the direction of radiation from the light source—by means of one common excitation filter.

Because of the joint evaluation of signals and reference signls which are derived from essentially identical components or component areas, a measured value will be obtained which is essentially independent of the configuration of the optical sensor and may be regarded as a standardized value. A still further embodiment of the invention provides that the signals of the photodetector may be standardized relative to the intensity of the excitation light by dividing them by the signals of the reference photodetector.

DESCRIPTION OF THE DRAWING

The following is a more detailed description of the invention as illustrated by the enclosed drawing in which

FIG. 1 is a section through a known kind of optical sensor as used for measuring or analyzing gases which are contained in preferably colourless gases or liquids, which gases or liquids are either contained in or flowing through a measuring chamber $3'$. Via excitation filters $2'$ a light source $1'$ illuminates a sensor element $4'$, causing it to give off fluorescent radiation. Intensity and wavelength of the fluorescent radiation will depend on the quantity of gas to be analyzed which is contained in the gas or liquid filled into the measuring chamber $3'$, since the sensor element $4'$ will change its emission properties according to how much gas to be analyzed it has picked up.

The fluorescence radiation given off by the sensor element $4'$ will reach, by way of emission filters $5'$ which filter out the excitation radiation, a photodetector $6'$ which is connected to an evaluation unit. This type of sensor will permit the oxygen content in respiratory gas to be determined with response times $t_{90}$ of less than 0.2 seconds.

DESCRIPTION OF THE PREFERRED EMBODIMENTS

Figure 1:
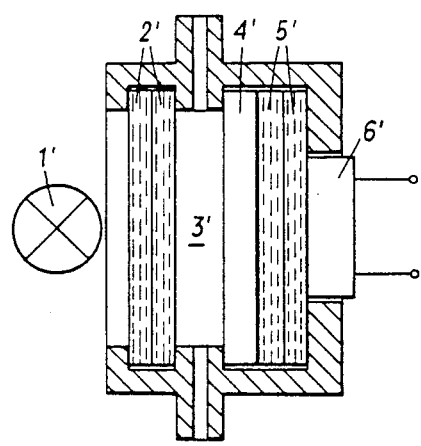
FIG. 1 presents the basic configuration of an optical sensor.
Figure 2:
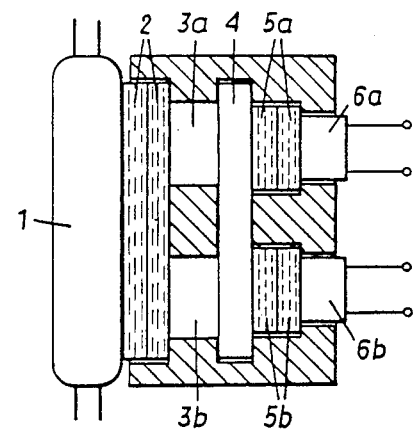
FIG. 2 is a schematical section through a sensor according to the present invention.

FIG. 2 shows an optical sensor designed according to the present invention. Via excitation filters 2 a light source 1 radiates both through a measuring chamber $3a$ onto a sample measuring element 4 and through a reference measuring chamber $3b$ onto another sensor area of the element 4. Basically, it would be possible to employ two sensor elements, i.e., one each for measuring chamber $3a$ and reference measuring chamber $3b$; the useof one single element 4 is preferred, however, since different areas of one and the same sensor element will exhibit fewer differences stemming from aging, manufacture and design than two separate sensor elements. The fluorescence radiation excited in the measuring element 4 in the area of measuring chamber $3a$ is transmitted to a photodetector $6a$ via emission filters $5a$, and the fluorescence radiation excited in the area of reference measuring chamber $3b$ in the measuring element 4, which will remain constant during the course of measurement is transmitted to a reference photodetector $6b$ via reference emission filters $5b$. Reference measurng chamber $3b$ contains a reference gas of constant composition which will allow the signals of the reference photodetector $6b$ to be used as a reference for the measurement signals of the photodetector $6a$. For evaluation of the signals arriving from the photodetector $6a$ and the reference photodetector $6b$, an evaluation unit 12 (FIG. 3) is used in which the signals will be processed against each other, e.g., divided or compared or related to one another in some other way, such that absolute values may be obtained.

In order to prevent further possible deviations of the values measured, or errors resulting from the configuration of the sensor, the light source 1 is placed symmetrically to measuring chamber $3a$ and reference measuring chamber $3b$. Besides, the excitation filters 2 for the measuring chamber $3a$ and the reference measuring chamber $3b$ are combined into one single filter serving both chambers. As is shown in FIG. 2, several excitation filters 2 and emission filters $5a$ or reference emission filters may be arranged one behind the other.

The measuring element 4 comprises a thin coat of a polymer material containing an oxygen indicator, which has been applied onto a rigid transparent carrier. On account of the excellent bond between the indicator membrane and the transparent carrier, the element 4 formed in this manner is characterized by great physical strength in spite of the thinness of the indicator membrane.

Since excitation and emission of fluorescence may be separated spectrally, colourless gaseous samples, as shown in FIG. 2, may be measured by a kind of "transillumination" method which will keep the optical paths short. The measuring chamber $3a$ or the reference measuring chamber $3b$ and the optical elements for the excitation and detection of fluorescence are centered on the optical axis one behind the other. With this arrangement, the excitation filters 2 and the measuring element 4 may be used as "walls" for the measuring chamber at the same time.

Optical sensors of the type shown here are mainly employed for determining the partial pressure of $O_2$ or $CO_2$ in respiratory gas, since the excitation radiation may easily be filtered out by the emission filters 5a or reference emission filters 5b. It is also possible to analyzed the gas content of liquids, however.

Figure 3:
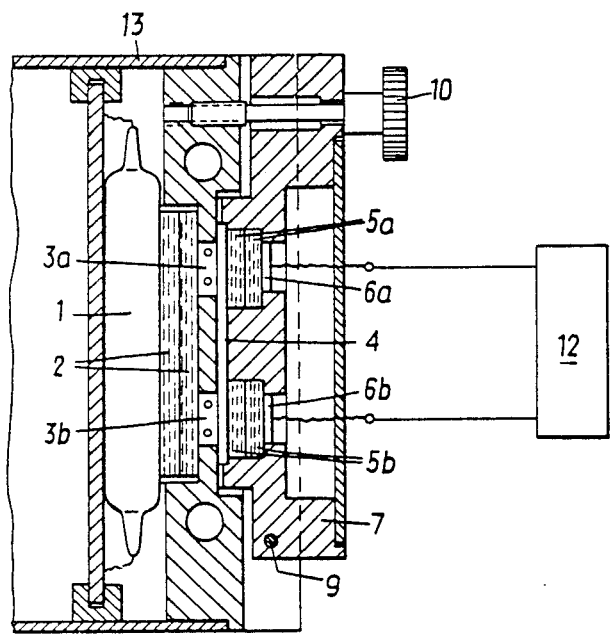
FIG. 3 is a section through a sensor for the analysis of respiratory gas.

FIG. 3 presents the design of a measuring device comprising an optical sensor for the analysis of respiratory gas. In a light housing 13 a light source 1, e.g., a gas discharge tube, is mounted whose light will reach the measuring chamber 3a and the reference measuring chamber 3b by way of excitation filters 2. Respiratoy gas is passed through measuring chamber 3a, the temperature of this gas being held constant in order to prevent the test results from being influenced by temperature fluctuations. The reference measuring chamber 3b contains respiratory gas, standard gas or air, whose composition is known and will remain constant during measurement. Whereas in measuring chamber 3a the oxygen partial pressure in respiratory gas is measured which is subject to changes, the oxygen partial pressure in reference measuring chamber 3b is maintained at a constant level and will serve as a reference.

On light housing 13 a sensor housing 7 is held which may be tilted around an axis 9 and which may be fastened in its operating position to housing 13 by means of screws 10, firmly pressing the measuring element 4 against the rear openings of the measuring chamber 3a and the reference measuring chamber 3b whose front openings are covered by the excitation filters 2. The sensor housing 7 contains the emission filters 5a, reference emission filters 5b, photodetectar 6a and reference photodector 6b, the latter two being connected to the evaluation unit 12. The temperature of sensor housing 7 and/or that of light housing 13 is held constant, for which purpose thermostat-controlled heating units are provided in housing 13 and/or sensor housing 7. It is essential that the temperatures in measuring chamber 3a and reference measuring chamber 3b should be the same.

In order to prevent any mutual interference, separate emission filters 5a and reference emission filters 5b are provided for measuring chamber 3a and reference measuring chamber 3b.

In the evaluation unit 12 the measurement signals may be evaluated by digital or analog methods. If the measurement signal of the photodetector 6a is divided by the reference signal of the reference photodetector 6b, a fluorescence signal is obtained which is standardized relative to the intensity of the excitation light.

I claim:

1. An optical sensor apparatus which has an operating mode and a non-operating mode and when in its operating mode can measure the partial pressure of a particular gas in a liquid or gaseous sample medium and when in its operating mode comprises
    a sample chamber for containing the liquid or gaseous sample medium which contains a particular gas whose partial pressure is to be measured, said sample chamber having first and second opposite sides,
    a separate reference chamber for containing a reference medium, said reference chamber having first and second opposite sides,
    a light source for radiating excitation light toward the first side of each of said sample chamber and said reference chamber,
    a unitary excitation filter positioned between said light source and the first side of both said sample chamber and said reference chamber, said unitary excitation filter covering the first side of both said sample chamber and said reference chamber and functioning to filter the excitation light from said light source which passes to each of said sample chamber and said reference chamber,
    a single fluorescent sensor element positioned to cover the second sides of both said sample chamber and said reference chamber, said single fluorescent sensor element including a first portion and a second portion and a first side and a second side, the first side of said first portion facing said sample chamber and the first side of said second portion facing said reference chamber, and the second sides of both first and second portions facing away from said sample chamber and said measuring chamber respectively,
    first and second separate emission filter means located on the second side of said single fluorescent sensor element, said first and second emission filter means having first sides which face said single fluorescent sensor element and second sides facing away therefrom, the first side of said first emission filter means facing the second side of said first portion of said single fluorescent sensor element and the first side of said second emission filter means facing the second side second portion of said single fluorescent sensor element, and
    first and second photodetectors respectively located on the second sides of said first and second emission filter means, said optical sensor apparatus operating such that rays of excitation light from said light source will pass through different areas of said unitary excitation filter, then through each of said sample chamber and said reference chamber, then into said first and second portions of said single fluorescent sensor element, thereby generating fluorescent radiation which is quenched in said first and second portions by the respective sample medium and reference medium, the fluoresent radiation generated in said first and second portions of said single fluorescent sensor element respectively then passing through said first and second emission filter means and respectively to said first and second photodetectors.

2. An optical sensor apparatus according to claim 1, wherein said light source is symmetrically positioned with respect to said sample chamber and said reference chamber.

3. An optical sensor apparatus according to claim 1, including a temperature control device for maintaining the temperature of said fluorescent sensor element constant.

4. An optical sensor apparatus according to claim 1, additionally comprising a sensor housing and a thermostat, add wherein said sample chamber and said reference chamber are maintained at the same constant temperature by said thermostat.

5. An optical sensor apparatus according to claim 1, further comprising a sensor housing and a light housing, wherein said sensor housing contains said single fluorescent sensor element, said first and second emission filter means, and said first and second photodetectors, and wherein said light housing contains said light source, said unitary excitation filter, said sample chamber and said reference chamber, wherein said sensor housing is pivotally attached to said light housing such that said sensor element and said light housing can be moved together to cause said optical sensor apparatus to be in its operating mode or moved apart to cause said optical sensor apparatus to be in its non-operating mode, and including means for fixedly connecting said sensor housing to said light housing when they are moved together.

6. An optical sensor apparatus according to claim 5, wherein said single fluorescent sensor element provides the second side of both said sample chamber and said reference chamber when said sensor housing and said light housing are moved together.

7. An optical sensor apparatus according to claim 1, wherein said single fluorescent sensor element further comprises a thin coat of polymer material containing an oxygen indicator which is applied to a transparent rigid carrier.

* * * * *